US00PP37021P2

(12) United States Plant Patent
Huber

(10) Patent No.: US PP37,021 P2
(45) Date of Patent: Oct. 14, 2025

(54) ***DAHLIA* PLANT NAMED 'LeeAnn's FDN79C'**

(50) Latin Name: *Dahlia hybrida*
Varietal Denomination: LeeAnn's FDN79C

(71) Applicant: LeeAnn Huber, Greencastle, PA (US)

(72) Inventor: LeeAnn Huber, Greencastle, PA (US)

(73) Assignee: Coseytown Flowers LLC, State Line, PA (US)

( * ) Notice: Subject to any disclaimer, the term of this patent is extended or adjusted under 35 U.S.C. 154(b) by 0 days.

(21) Appl. No.: 19/028,191

(22) Filed: Jan. 17, 2025

(51) Int. Cl.
*A01H 5/02* (2018.01)
*A01H 6/00* (2018.01)

(52) U.S. Cl.
USPC ..... Plt./321
CPC ..... *A01H 6/00* (2018.05)

(58) Field of Classification Search
USPC ..... Plt./321
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Dahlia* plant named 'LeeAnn's FDN79C' is disclosed, characterized by a strong, upright growth habit, combined with free and early flowering. Flowers are held above the foliage canopy and have a consistent quality throughout the growing season. Flowering stems have an above average strength with a firm blossom attachment. Flower color is a unique shade of bright magenta purple which is new to the market. Inflorescences have strong postproduction quality. The new variety is a *Dahlia* typically produced for cut flower purposes, or garden or landscape.

2 Drawing Sheets

Figure 1:
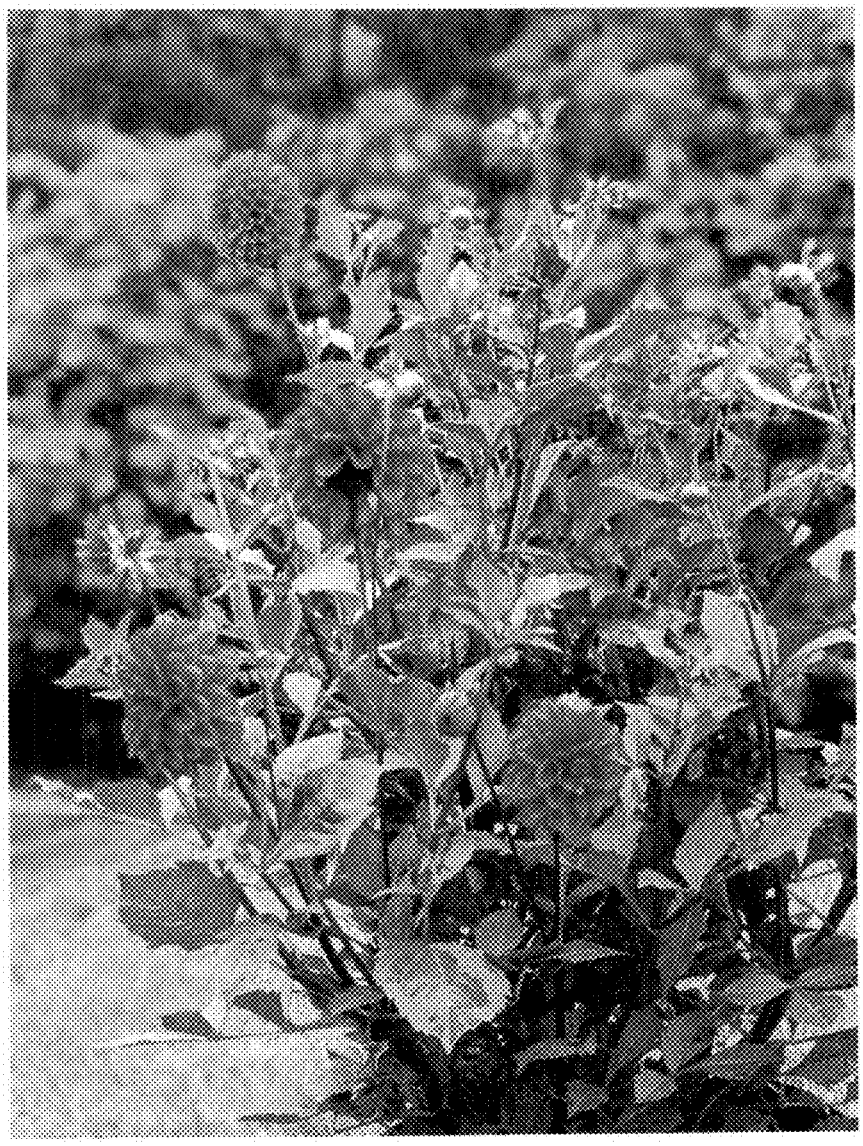

Latin name of the genus and species: *Dahlia hybrida.*
Variety denomination: 'LeeAnn's FDN79C'.

BACKGROUND OF THE INVENTION

The new *Dahlia* cultivar is a product of a planned breeding program conducted by the inventor, in Greencastle, Pennsylvania. The objective of the breeding program was to produce new *Dahlia* varieties with improved performance in open field conditions and produce cut flowers suitable for transport and sale. The open-pollination resulting in this new variety was made during 2018.

The seed parent is the unpatented, variety of *Dahlia* 'Snoho Jojo'. The pollen parent is unidentified. Seed from 'Snoho Jojo' was collected in 2018 and grown in a cultivated garden area in 2019. 'LeeAnn's FDN79C' was intentionally selected from the seedlings that resulted based on the criteria of stem length and strength, upright growth habit, inflorescence attachment, ray floret count, and inflorescence color.

Asexual reproduction of the new cultivar was first performed by vegetative cuttings by the inventor in Greencastle, Pennsylvania in the Spring of 2020 and has shown that the unique features of this cultivar are stable and reproduced true to type in successive generations.

SUMMARY OF THE INVENTION

The cultivar 'LeeAnn's FDN79C' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LeeAnn's FDN79C'. These characteristics in combination distinguish 'LeeAnn's FDN79C' as a new and distinct *Dahlia* cultivar:

1. Strong, upright growth habit requiring minimal to no field support.
2. Free branching.
3. Early flowering.
4. Consistency of inflorescence quality throughout the growing season.
5. Inflorescence held above the leaf canopy.
6. Above average stem strength.
7. Firm inflorescence attachment.
8. Unique bright, magenta purple ray floret color, new to the US cut flower market.
9. Strong postproduction inflorescence quality.
10. Dark flower stems and dark green foliage.

PARENT COMPARISON

Plants of the new cultivar 'LeeAnn's FDN79C' are similar to plants of the seed parent, in some horticultural characteristics, however, plants of the new cultivar 'LeeAnn's FDN79C' differ in the following;

1. Inflorescence color of the new cultivar is bright, magenta purple; inflorescence color of the seed parent is coral pink.
2. Inflorescence form of the new cultivar is decorative; inflorescence form of the seed parent is ball.
3. Inflorescence color of the new cultivar remains stable throughout the growing season and location; inflorescence color of the seed parent changes more readily with seasonal and environmental changes.

The pollen parent cannot be identified with certainty.

COMMERCIAL COMPARISON

Plants of the new cultivar 'LeeAnn's FDN79C' are comparable to the cultivar *Dahlia* 'LeeAnn's FD61A', U.S. Plant patent application Ser. No. 18/999,438. The two *Dahlia* cultivar are similar in most horticultural characteristics; however, the new cultivar 'LeeAnn's FDN79C' differs in the following:

1. Inflorescences of the new cultivar have on average 104 ray florets arranged in 13 whorls; inflorescences of 'LeeAnn's FD47C' has on average 160 ray florets arranged in 11 whorls.
2. Inflorescence stem color of the new cultivar is dark purple (Greyed-Purple 187A); flower stem color of this comparator is green.
3. Plants of the new cultivar have not been observed to set seed; plants of this comparator have been observed to produce seed infrequently.

BRIEF DESCRIPTION OF THE PHOTOGRAPHS

The accompanying photograph in FIG. 1 illustrates in full color a typical flowering plant of 'LeeAnn's FDN79C' grown outdoors, in the ground under cut flower production conditions. Age of the plant photographed is approximately 17 weeks from a rooted cutting.

Figure 2:
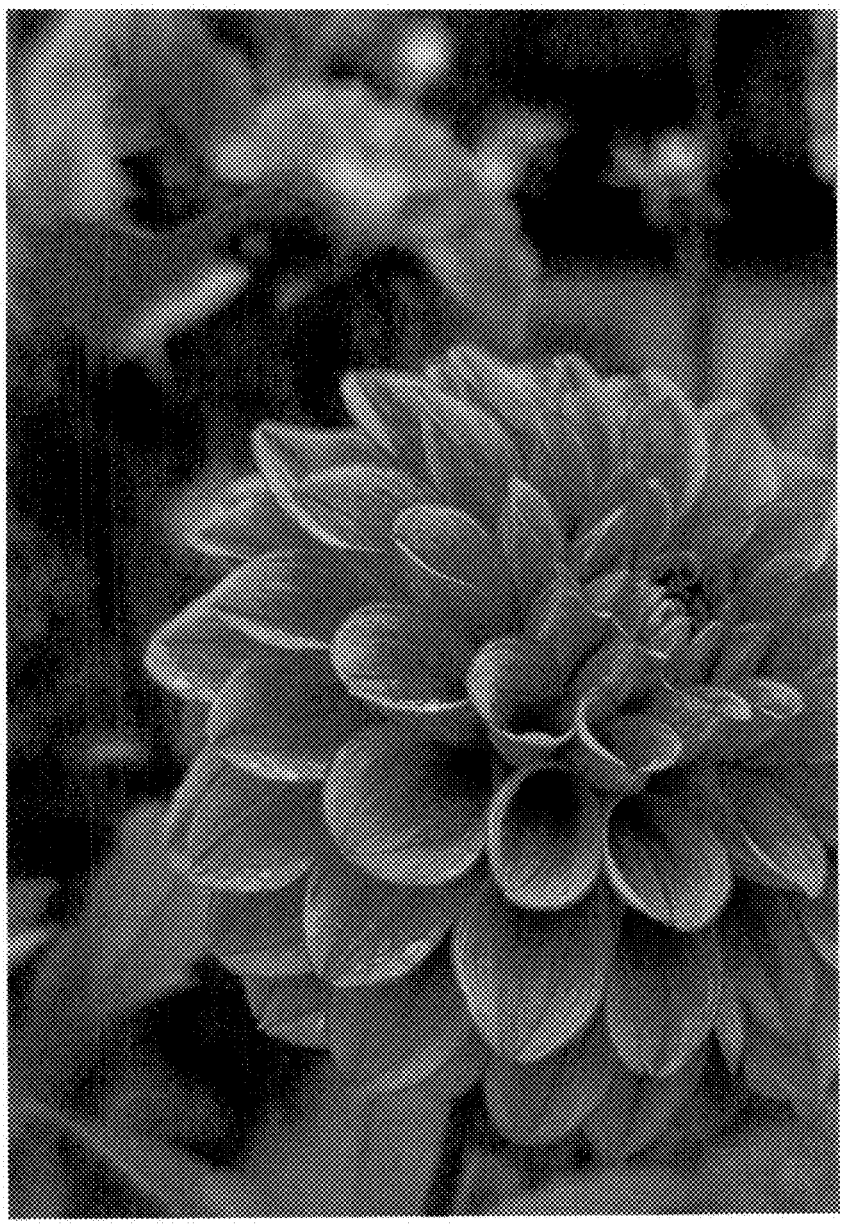

FIG. 2 illustrates a close-up of the inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society R.H.S. Colour Chart 2015 except where general terms of ordinary dictionary significance are used. The following observations and measurements describe 'LeeAnn's FDN79C' plants grown outdoors, in production cut flower rows in Greencastle, PA. The average growing season for outdoor cut flower production runs from May through mid-October or 24 weeks. The terminal bud is pinched off the *Dahlia* around 4-6 weeks of age. Temperatures ranged from about 23° C. to 39° C. during the day and 7° C. to 23° C. at night. General light conditions are bright, normal sunlight. Botanical data was collected between May and September. Measurements and numerical values represent averages of typical plant types. Age of the plants described is approximately 17 weeks from a rooted cutting Botanical classification: *Dahlia hybrida* 'LeeAnn's FDN79C'.

PROPAGATION

Typical propagation method: Vegetative terminal cuttings or tubers.

Time to initiate roots, terminal cutting: (March) Winter: 5 to 18 days at approximately 18° C.

Root description: Freely branching, fine rootlets with canescent hairs

PLANT

Plant type: Herbaceous flowering perennial.

Growth habit: Upright growth habit that branches freely producing numerous strong stalks holding inflorescences above foliage. Vigorous growth and regrowth after continuous inflorescence harvesting. Short lateral branch internodes that readily branch produce a strong stout plant requiring minimal to no growth supports.

Height: 89.5 cm.

Plant spread: 45.2 cm.

Growth rate: Vigorous.

Branching characteristics: Free-branching, lateral branches on average 47.8 cm long.

Characteristics of primary lateral branches:

*Diameter.*—Lateral Branch Base Diameter: about 12.2 mm. Lateral Branch Apex Diameter: about 14.5 mm.

*Color.*—Greyed-Purple 187A tinted Green 143B.

*Texture.*—Smooth, glabrous with minimal longitudinal sulcate grooves.

*Strength.*—Exceptional, no flex or give.

Internode length: $2^{nd}$ Internode Length: about 74.5 mm.

FOLIAGE

Leaf:

*Arrangement.*—Opposite. Single or compound with 3, 5, or 7 leaflets.

Leaflets:

*Shape of blade.*—Ovate.

*Apex.*—Apiculate.

*Base.*—Attenuate.

*Margin.*—Serrated.

*Texture of all surface.*—Glabrous.

*Pubescence.*—none present.

*Color.*—Young foliage upper side: RHS 137B. Young foliage under side: RHS 138B. Mature foliage upper side: RHS NN137A. Mature foliage under side: RHS 147B.

Size:

*Length.*—Leaflet: About 33 mm. Single leaves About 77 mm. Compound leaves with three leaflets: About 95 mm. Compound leaves with five leaflets: About 126 mm. Compound leaves with seven leaflets: About 170 mm.

*Width.*—Leaflet: About 25 mm. Single leaves about 38 mm. Compound leaves with three leaflets: about 117 mm. Compound leaves with five leaflets: about 139 mm. Compound leaves with seven leaflets: About 194 mm.

*Venation.*—Type: Pinnate. Venation color upper side: Green 143C. Venation color under side: Green 143C.

Petiole:

*Single leaves.*—No petiole. Length: Compound leaves with three leaflets: about 32.7 mm. Compound leaves with five leaflets: about 33.5 mm. Compound leaves with seven leaflets: about 46.2 mm. Diameter: Compound leaves with three leaflets: about 2.8 mm. Compound leaves with five leaflets: about 3.7 mm. Compound leaves with seven leaflets about: 4.4 mm.

*Color.*—Upper surface: Green NN137A filtered through Greyed-Purple 187A. Lower Surface: Yellow-Green 146D.

*Texture.*—Glabrous all surfaces.

Rachis:

*Length.*—5 to 11 cm.

*Diameter.*—3.5 to 5.5 mm.

*Color.*—Upper surface: Green 137A. Lower Surface: Yellow-Green 146D.

*Texture.*—Glabrous all surfaces.

Stipule: Not present.

INFLORESCENCE

Natural flowering season: During frost free days and nights beginning late April/early May through end of September/October.

Days to flowering from rooted cutting: Plants begin to bloom around 70 days after planting; continuously blooming until the season ending frost in Pennsylvania while maintaining good ray floret count and inflorescence form.

Inflorescence and flower type and habit: Fully double formal decorative *Dahlia* with ray and disc florets positioned acropetally on a capitulum. Inflorescences positioned above the foliage on very strong peduncles with an upright to 45° blossom position.

Inflorescences per plant: On average 10 to 12 inflorescences and buds at one time.

Rate of flower opening: 15 to 18 days from bud to fully opened flower.

Flower longevity on plant: Inflorescences maintain good substance (attractive color with good moisture content) on the plant for about 16 days.

Flower longevity as a cut flower: For about 6-7 days as a cut flower (fresh water at room temperature).

Fragrance: None.

Persistent or self-cleaning: Self Cleaning.

Inflorescence:
- *Diameter*.—Approximately About 82.3 mm.
- *Depth*.—Approximately About 50.5 mm.
- *Width of disc* (*if present*).—About 9.4 mm.
- *Depth of disc* (*if present*).—7 mm.
- *Receptacle diameter*.—About 15.6 mm.

Bud:
- *Shape*.—Oblate.
- *Length*.—64 mm.
- *Diameter*.—12 mm.
- *Color*.—RHS Yellow-Green 144B.
- *Appearance*.—Semi-glossy.
- *Texture*.—Glabrous.

Ray florets:
- *Number of ray florets per inflorescence*.—Average 163.
- *Length*.—About 31.8 mm.
- *Width*.—About 18.3 mm.
- *Shape*.—Obovate.
- *Apex*.—Obtuse.
- *Base*.—Attenuate.
- *Margin*.—Entire.
- *Aspect*.—Initially upright to roughly perpendicular to the peduncle to cupped when completely reflexed.
- *Texture*.—Upper surface-Smooth, velvety. Lower surface-Smooth, velvety.

Color:
- *Ray florets*.—Upper surface at first opening: Apex Purple N79C, Mid-section NN78B streaked Purple NN78A, Base Red-Purple NN74A. Upper surface at maturity: NN78B and NN78C streaked Purple N79C. Under surface at first opening: Purple N79C with stripes of White N155C. Under surface at maturity: NN78B and NN78C streaked Purple N79C.

Disc florets:
- *Number of disc florets per inflorescence*.—About 61.
- *Shape*.—Tubular.
- *Apex*.—Acute.
- *Length*.—About 7.4 mm.
- *Diameter, base*.—About 1.26 mm.
- *Texture*.—Upper and lower surfaces-Smooth, glabrous.
- *Margin*.—Entire.
- *Color*.—Apex Yellow 9A, midsection Yellow-Orange 23A, base 9C.

Phyllaries:
- *Quantity per inflorescence*.—Average 8 arranged in a single whorl.
- *Length*.—Approximately 17.2 mm.
- *Width*.—Approximately 4.7 mm.
- *Shape*.—Oval.
- *Texture*.—Upper and lower surfaces-Smooth, glabrous, waxy.
- *Apex shape*.—Acute.
- *Base*.—Truncate.
- *Margin*.—Entire.
- *Color*.—Upper Surface Green 139B, Lower Surface Green 139B with 187A stripes.

Peduncle (measured from terminal peduncle):
- *Length*.—21.3 cm.
- *Diameter*.—4.5 to 6.5 mm.
- *Angle*.—Completely upright.
- *Strength*.—Exceptional with no bend or give.
- *Texture*.—Glabrous.
- *Color*.—RHS Greyed-Purple 187A.

REPRODUCTIVE ORGANS

Disc florets:

Androecium:
- *Stamens*.—5.
- *Anther shape*.—Linear.
- *Anther length*.—Approximately 4.7 mm.
- *Anther color*.—Near RHS Yellow-Orange 21A.
- *Pollen quantity*.—Scant.
- *Pollen color*.—21A.

Gynoecium:
- *Pistil number*.—1.
- *Pistil length*.—Approx. 24.2 mm.
- *Stigma shape*.—Bifurcate.
- *Stigma form*.—Plumose.
- *Stigma length*.—About 3.1 mm.
- *Stigma width*.—About 0.8 mm.
- *Stigma color*.—Near RHS Yellow-Orange 15A.
- *Style length*.—15 mm.
- *Style color*.—Yellow 2D.
- *Ovary position*.—Inferior.
- *Ovary shape*.—Truncate.
- *Ovary color*.—Green-White 157D.
- *Ovary length*.—About 2.4 mm.
- *Ovary width*.—About 1.7 mm.

Ray florets: No reproductive structures present

OTHER CHARACTERISTICS

Fruit/seed: No seed production observed.

Disease/pest resistance: Neither resistance nor susceptibility to normal diseases and pests of *Dahlia* has been observed.

Weather and climate performance: Plants of the new *Dahlia* have excellent tolerance to heat and high UV index, resisting wilting and fading in field grown conditions. Daylight length has minimal effects on bud and bloom production, maintaining cut flower output into late season light and weather conditions.

Temperature range: Grown in any zone as an annual. Can be overwintered in Zone 6 and 7 with protective mulch. Can be perennialized in zones 8 and above.

What is claimed is:

1. A new and distinct cultivar of *Dahlia* plant named 'LeeAnn's FDN79C' as herein illustrated and described.

* * * * *